United States Patent
Kuno et al.

(10) Patent No.: US 7,439,013 B2
(45) Date of Patent: Oct. 21, 2008

(54) BIOCOMPATIBLE POLYMER AND FILTER FOR SELECTIVELY ELIMINATING LEUCOCYTES USING THE SAME

(75) Inventors: Susumu Kuno, Oita (JP); Hirokazu Onodera, Oita (JP); Masami Sakurai, Oita (JP)

(73) Assignee: Asahi Kasei Kuraray Medical Co., Ltd., Tokyo (JP)

( * ) Notice: Subject to any disclaimer, the term of this patent is extended or adjusted under 35 U.S.C. 154(b) by 293 days.

(21) Appl. No.: 10/518,351

(22) PCT Filed: Jun. 17, 2003

(86) PCT No.: PCT/JP03/07687

§ 371 (c)(1),
(2), (4) Date: Aug. 30, 2005

(87) PCT Pub. No.: WO03/106518

PCT Pub. Date: Dec. 24, 2003

(65) Prior Publication Data

US 2006/0073467 A1 Apr. 6, 2006

(30) Foreign Application Priority Data

Jun. 17, 2002 (JP) ............................ 2002-176332
Jun. 17, 2002 (JP) ............................ 2002-176333

(51) Int. Cl.
*A01N 1/02* (2006.01)
*B01J 20/26* (2006.01)
*B01D 11/00* (2006.01)
(52) U.S. Cl. ........................... 435/2; 210/645; 502/402
(58) Field of Classification Search ................ None
See application file for complete search history.

(56) References Cited

U.S. PATENT DOCUMENTS 5,407,581 A * 4/1995 Onodera et al. ............. 210/654

FOREIGN PATENT DOCUMENTS

| JP | 56-168623 | 12/1981 |
| JP | 1-256971 | 10/1989 |
| JP | 6-72759 | 3/1994 |
| JP | 6-184508 | 7/1994 |
| JP | 7-25776 | 1/1995 |
| JP | 10-230014 | 2/1998 |
| JP | 2000-185094 | 7/2000 |
| JP | 2000-245833 | 9/2000 |
| JP | 2001-300221 | * 10/2001 |
| JP | 2001-316422 | 11/2001 |
| WO | WO 00/61646 | 10/2000 |
| WO | 03/033053 | * 4/2003 |
| WO | WO 03/033053 | 4/2003 |

* cited by examiner

*Primary Examiner*—Sandra E. Saucier
(74) *Attorney, Agent, or Firm*—Young & Thompson (57) ABSTRACT

It is intended to provide a polymer which is scarcely eluted, has a high biocompatibility and is useful in a filter for selectively eliminating leucocytes. It is also intended to provide a filter for selectively eliminating leucocytes, a filtration apparatus for selectively eliminating leucocytes and a system for selectively eliminating leucocytes, each having the above-described polymer. The above objects can be achieved by providing a polymer which comprises from 8% by mol to 45% by mol of a unit originating in a polymerizable monomer having a polyalkylene oxide chain, from 30% by mol to 90% by mol of a unit originating in a polymerizable monomer having a hydrophobic group, and from 2% by mol to 50% by mol of a unit originating in polymerizable monomer having a hydroxyl group.

36 Claims, 2 Drawing Sheets

BIOCOMPATIBLE POLYMER AND FILTER FOR SELECTIVELY ELIMINATING LEUCOCYTES USING THE SAME

TECHNICAL FIELD

The present invention relates to a polymer having excellent biocompatibility. More particularly, the present invention relates to a polymer that can be used for a filter for selectively removing leukocytes which exhibits only slight adherence with platelets and can selectively remove leukocytes from blood. The present invention also relates to a filter material for selectively removing leukocytes in blood during transfusion or extracorporeal circulation, an apparatus for selectively removing leukocytes, a system for selectively removing leukocytes, and a method of treating diseases using the system.

BACKGROUND ART

Following the progress of immunology and blood transfusion in recent years, component transfusion in which only blood components required for treating various diseases are transfused has become more popular than conventional whole blood transfusion. Blood component transfusion is an outstanding transfusion treatment exhibiting a high curative effect, while mitigating the load on patients during transfusion. Various blood preparations used for the blood component transfusion, such as concentrated erythrocytes, concentrated platelets, and platelet poor plasma, are prepared by centrifuging whole blood obtained by donation. However, it has become known that side reactions are induced after transfusion due to the leukocytes contained in these blood preparations because the blood preparations obtained by centrifugation contain many leukocytes. The side reactions after transfusion include comparatively slight side reactions, such as headache, nausea, a chill, and a non-hemolytic exothermic reaction, as well as serious side reactions such as induction of graft versus host (GVH) reaction to a patient with an immune disorder in which the transfused leukocytes has a death-inducing effect on the skin and internal organs of the recipient, infection by viruses present in leukocytes such as cytomegalovirus infection, and alloantigen sensibilization. Removing leukocytes from the blood preparations is effective in preventing such side reactions after transfusion.

There has been an increasing demand for the technology of removing leukocytes from patient's peripheral blood for medical treatment of systemic erythematodes, chronic or malignant rheumatoid arthritis, Behcet's disease, idiopathic thrombo-cytopenic purpura, autoimmune hepatitis, chronic ulcerative colitis, Crohn's disease, atopic dermatitis, rapidly progressive glomerulonephritis, and systemic inflammatory response syndrome, and for the purpose of immune suppression before transplant. Leukocyte removal is practiced also in the field of heart surgery, wherein leukocytes are removed from the blood perfused after coronary-artery bypass surgery to mitigate a hindrance effect by activated leukocytes.

Methods for removing leukocytes from blood are broadly classified into a centrifuge separation method, making use of differences in the specific gravity of blood components, and a filter method using a fibrous medium such as non-woven fabric or a porous sponge-like material having three-dimensional continuous pore networks as a filter. The filter method is more popular due to higher leukocyte removal efficiency, simple procedure, and lower cost.

Polymer materials consisting these leukocyte-removal filters are generally hydrophobic and cause other useful blood components such as platelets to adhere when removing leukocytes. It has been difficult to achieve a balance between the leukocyte-removal efficiency and the platelet recovery efficiency. Development of a material that can selectively remove leukocytes, while allowing platelets to pass through, has been strongly desired, particularly for patients with a disease, in which a decrease in platelets is undesirable, such as idiopathic thrombocytopenic purpura or autoimmune hepatitis.

When an aqueous-type liquid containing platelets such as blood is caused to come in contact with a material, the higher the hydrophilicity of the surface of the material, the more difficult it is for the platelets to become activated and the easier it is for a water layer to be formed on the material surface by the hydrogen bond of water and the material, whereby adsorption of platelets and hydrophobic proteins can be inhibited. Therefore, various hydrophilic polymers have been developed to modify the surface of materials and methods for introducing such polymers onto the surface of materials by graft polymerization or coating are known in the art. JP-A 2000-245833 discloses a filter material for selectively removing leukocytes. The material allows erythrocytes and platelets to pass through, but does not allow leukocytes to pass through. In the filter material, the above problems have been overcome by coating a hydrophilic polymer onto the material forming the filter. One possible problem with the coated filter material is elution of the hydrophilic polymer from the surface. Although the possibility of the polymer elution into an aqueous solution is very low, a material with a smaller risk of elution has been desired for use in processing of a large amount of blood, such as that used for extracorporeal circulation, to ensure stability of the filter material when it is kept in contact with an aqueous solution such as blood for a long time.

JP-A 07-25776 discloses a filter material coated with a polymer having both hydrophobic groups and hydrophilic polyethylene oxide chains. This is a filter material with a reduced risk of polymer elution by decreasing the solubility of the polymer in an aqueous solution by introducing hydrophobic groups into the polymer. However, since the polymer has both hydrophobic groups and hydrophilic groups having opposite properties each other in the polymer molecule, the action of hydrophobic portions through which the polymer is caused to adhere to the filter supporting body which consists the filter material is reduced. It has, therefore, been difficult to ensure a balance between filter performance and elution properties using this technology alone. The inventors of the present invention examined this technology using a polymer made from methyl methacrylate and methoxypoly(ethylene glycol methacrylate) having polyethylene oxide chains. As a result, the present inventors have found that aqueous solutions become turbid due to polymer elution.

The present inventors have further found that a specific removing material surface can absorb viruses, remove leukocytes, and recover platelets and filed a patent application on the invention covering this finding (PCT/JP 02/10766, WO 03/033035). Although this prior patent application describes the same polymer as the polymer of the present invention as an example of the polymer for forming a specific surface, the prior invention differs from the present invention in that the claimed filter removes viruses simultaneously with leukocytes. In addition, the inventors of the present invention coated a specific supporting body with the polymer described in the prior application as one embodiment, of which the conditions of polymerization and purification differ from those applied to the present invention, and evaluated elution of the polymer. As a result, the present inventors have found that a slight degree of elution occurred, although the degree was not so remarkable as to cause the test solution to become turbid. It is needless to mention that it is more desirable to further suppress the elution taking into consideration the application of the filter in a medical treatment.

There have been no high performance polymers used for filters for selective removal of leukocytes exhibiting both high safety and high blood filtration performance at the same time.

DISCLOSURE OF THE INVENTION

An object of the present invention is to provide a novel polymer having an extremely low elution property and excellent biocompatibility, useful as a filter for selective removal of leukocytes which can selectively remove leukocytes from various bloods, particularly from whole blood, while preventing adsorption of platelets as much as possible. Specifically, the present invention provides a novel polymer that can be effectively used for platelet transfusion or extracorporeal circulation for leukocyte removal, excelling in biocompatibility, exhibiting only a low adsorption to platelets, and having a low elution property.

Other objects of the present invention are to provide a filter material for selective removal of leukocytes, a filter apparatus for selective removal of leukocytes, and a system for selective removal of leukocytes using the above polymer.

As a result of extensive studies, the present inventors have found that a polymer comprising a unit originating from a polymerizable monomer having a polyalkylene oxide chain, a unit originating from a polymerizable monomer having a hydrophobic group, and a unit originating from a polymerizable monomer having a hydroxyl group at a specific ratio surprisingly exhibits remarkably low elution property, excellent biocompatibility, particularly low adsorption to platelets, and excellent selective leukocyte removal capability. This finding has led to the completion of the present invention.

Specifically, the present invention provides a biocompatible polymer comprising 8-45 mol % of a unit originating from a polymerizable monomer having a polyalkylene oxide chain, 30-90 mol % of a unit originating from a polymerizable monomer having a hydrophobic group, and 2-50 mol % of a unit originating from a polymerizable monomer having a hydroxyl group, wherein the total of the three types of monomer units is 100 mol %.

In the present invention, a more excellent elution property has been confirmed to be obtained if the weight average molecular weight of the polymer is in the range from 100,000 to 3,000,000.

BEST MODE FOR CARRYING OUT THE INVENTION

The polyalkylene oxide chain used in the present invention refers to a repeating structure in which an alkyl group and an oxygen atom bond alternately. The polyalkylene oxide chains with an alkyl group having 2-4 carbon atoms, such as a polyethylene oxide chain, polypropylene oxide chain, and polybutylene oxide chain, are preferable. The polyalkylene oxide chain in the polymer exhibits a high platelet adsorption preventing effect due to the outstanding compatibility with blood possessed by the polyalkylene oxide chain.

The repeating number of the alkylene oxide chain used in the present invention is preferably from 2 to 10. If the number of repetitions is less than 2, it is difficult to obtain a sufficient platelet adsorption preventing effect. If the number of repetitions is more than 10, the polymer becomes less adhesive to the filter supporting body, thereby increasing a tendency of the polymer eluting more easily. The number of repetitions is preferably 2 to 6, and more preferably 2 to 4.

Examples of the polymerizable monomer having the polyalkylene oxide chain include, but are not limited to, methoxydiethylene glycol (meth)acrylate, ethoxydiethylene glycol (meth)acrylate, methoxydipropylene glycol (meth)acrylate, ethoxydipropylene glycol (meth)acrylate, methoxytriethylene glycol (meth)acrylate, methoxytripropylene glycol (meth) acrylate, ethoxytriethylene glycol (meth)acrylate, ethoxytripropylene glycol (meth)acrylate, methoxytetraethylene glycol (meth)acrylate, methoxytetrapropylene glycol (meth)acrylate, ethoxytetraethylene glycol (meth)acrylate, thoxytetrapropylene glycol (meth)acrylate, ethoxydiethylene glycol vinyl ether, ethoxydiethylene glycol vinyl ether, methoxytriethylene glycol vinyl ether, and ethoxytriethylene glycol vinyl ether. Of these, (meth)acrylate having a polyethylene glycol chain such as methoxydiethylene glycol (meth) acrylate, ethoxydiethylene glycol (meth)acrylate, methoxytriethylene glycol (meth)acrylate, ethoxytriethylene glycol (meth)acrylate, methoxytetraethylene glycol (meth) acrylate, and ethoxytetraethylene glycol (meth) acrylate are preferably used due to the high platelet adsorption preventing effect. Methoxydiethylene glycol (meth)acrylate is most preferable from the viewpoint of easy availability, easy handling, easy polymerization, and the like. The (meth)acrylate in the present invention refers to acrylate or methacrylate, or both.

It is necessary for the polymer of the present invention to contain the unit originating from the polymerizable monomer having a polyalkylene oxide chain in an amount from 8 mol % to 45 mol %. If less than 8 mol %, the platelet adsorption preventing effect of the polyalkylene oxide chain is insufficient, resulting in reduced platelet recovery performance. If more than 45 mol %, the hydrophobicity of the polymer decreases, giving rise to easy elution of the polymer when coming into contact with an aqueous solution such as blood. The amount of the unit is preferably from 20 mol % to 40 mol %, and more preferably from 25 mol % to 35 mol %.

The term "unit" in the present invention refers to a minimum recurring unit in a polymer molecule originating from respective polymerizable monomers. For example, in the case of the addition polymerization of a polymerizable monomer of a vinyl compound with the formula $CH_2=CXY$ (wherein X is H or a substituent other than H and Y is a substituent other than X) by simply opening the double bond, the minimum recurring unit is —($CH_2$—CXY)—. In the case where the polymer is synthesized by polycondensation from a polymer precursor of the formula A-(R)-B, wherein R indicates a part not released in the polymerization and A and B are releasable parts during the polymerization reaction, —(R)— is the minimum recurring unit.

The term "polymerizable monomer having a hydrophobic group" in the present invention refers to a polymerizable monomer having solubility in water at 20° C. of 0 wt % or more and less than 50 wt %, and not containing a polyalkylene oxide chain and a hydroxyl group in the molecule. The unit originating from a polymerizable monomer having a hydrophobic group has effects of decreasing the solubility of the polymer in an aqueous solution, preventing elution of the polymer, and increasing leukocyte removal performance.

The solubility can be determined by a known method such as a dew point method, thermal analysis, electric method comprising measurement of the electromotive force or electric conductivity of the solution, gas chromatography analysis, and tracer method in the case where the monomer is a solid. When the monomer is a liquid, the solubility can be determined by, in addition to the methods applied to a solid monomer, a capacitance method, light scattering method, vapor pressure method, or the like, all of which are known in the art. As simpler method, when the monomer has a boiling point sufficiently higher than the boiling point of water, a method of vaporizing water from a saturated solution of the monomer and measuring the weight of the residue can be used.

As examples of the above-mentioned polymerizable monomer having a hydrophobic group, styrene, methylstyrene, butyl (meth)acrylate, isobutyl (meth)acrylate, propyl (meth)acrylate, isopropyl (meth)acrylate, ethyl (meth)acrylate, methyl (meth)acrylate, phenyl (meth)acrylate, ethylhexyl (meth) acrylate, and vinyl acetate can be given. Of these, alkyl (meth)acrylates such as butyl (meth)acrylate, isobutyl (meth)acrylate, propyl (meth)acrylate, isopropyl (meth)acrylate, ethyl (meth)acrylate, and methyl (meth)acrylate are preferably used due to their adequately hydrophobic and easily polymerizable properties. Methyl (meth)acrylate is most preferable from the viewpoint of high biological safety.

It is necessary for the polymer of the present invention to contain the unit originating from the polymerizable monomer having a hydrophobic group in an amount from 30 mol % to 90 mol %. If less than 30 mol %, the hydrophobicity of the polymer decreases, giving rise to easy elution of the polymer when coming into contact with an aqueous solution such as blood. If more than 90 mol %, the hydrophobicity of the polymer increases, giving rise to increased adsorption of platelets to the surface of the filter material. The amount of the unit is preferably from 35 mol % to 80 mol %, and more preferably from 40 mol % to 70 mol %.

The term "polymerizable monomer containing a hydroxyl group" as used in the present invention refers to a polymerizable monomer having a hydroxyl group, but not containing a polyalkylene oxide chain in the molecule. For example, polymerizable monomers containing an alkyl hydroxyl group such as 2-hydroxyethyl (meth)acrylate, 2-hydroxypropyl (meth)acrylate, 3-hydroxypropyl (meth)acrylate, 2-hydroxyisobutyl (meth)acrylate, 3-hydroxyisobutyl (meth)acrylate, 2-hydroxybutyl (meth)acrylate, 3-hydroxybutyl (meth)acrylate, and 4-hydroxybutyl (meth)acrylate are preferably used.

It is necessary for the polymer of the present invention to contain the unit originating from the polymerizable monomer having a hydroxyl group in an amount from 2 mol % to 50 mol %. If less than 2 mol %, the hydrophilicity of the polymer decreases, giving rise to increased adsorption of platelets to the surface of the filter material. If more than 50 mol %, the hydrophobicity of the polymer decreases, giving rise to easy elution of the polymer when coming into contact with an aqueous solution such as blood. The amount of the unit is preferably from 5 mol % to 40 mol %, and more preferably from 10 mol % to 30 mol %.

The content ratio of the unit originating from the polymerizable monomer having a hydroxyl group to the unit originating from the polymerizable monomer having a hydrophobic group in the polymer of the present invention is preferably from 0.05 to 1. The content ratio in the present invention is a value obtained by dividing the mol content of the unit originating from the polymerizable monomer having a hydroxyl group by the mol content of the unit originating from the polymerizable monomer having a hydrophobic group in the polymer. If the content ratio is less than 0.05, the hydrophilicity provided by hydroxyl groups is canceled by hydrophobic groups and the hydrophilicity of the polymer decreases, giving rise to increased adsorption of platelets to the surface of the filter material. If more than 1, the elution preventive effect of the hydrophobic groups is canceled by hydroxyl groups and hydrophobicity of the polymer decreases, giving rise to easy elution of the polymer when coming into contact with an aqueous solution such as blood. The content ratio is preferably from 0.1 to 0.9, and more preferably from 0.15 to 0.8.

The polymerizable monomer having a hydroxyl group used in the polymer of the present invention preferably has solubility in water at 20° C. in the range from 3 wt % or more, but less than 50 wt %. Due to the moderate hydrophilic and hydrophobic properties, the polymerizable monomer having a hydroxyl group provides the polymer with the effect of preventing adsorption of platelets and hydrophobic proteins together with the polyalkylene oxide chain, and, at the same time, the effect of preventing elution of the polymer together with a unit originating from strong hydrophobic polymerizable monomers. As the polymerizable monomer containing a hydroxyl group and having the above-mentioned solubility, 2-hydroxypropyl (meth)acrylate and 2-hydroxyisobutyl (meth)acrylate are preferably used due to their moderate hydrophilic and hydrophobic properties. Of these, 2-hydroxyisobutyl (meth)acrylate is most preferable from the viewpoint of the moderate hydrophilic properties.

The chemical composition of a polymer can be determined by extracting the polymer using an appropriate solvent which does not dissolve the supporting body of the filter and analyzing the extract by a known method such as NMR spectrum, IR spectrum, and elemental analysis. When the polymer is not dissolved, in addition to the above-mentioned methods, known surface analytical methods such as X-ray photoelectron spectroscopy (ESCA) and a method of using an electron probe X-ray microanalyser (EPMA) can be used.

The polymer of the present invention preferably has a weight average molecular weight (Mw) in the range of 100,000 to 3,000,000. If the Mw is less than 100,000, the molecular weight of the polymer decreases when the polymer is sterilized, particularly by radiation, giving rise to an increase in the eluted amount. If the weight average molecular weight (Mw) is more than 3,000,000, solubility of the polymer in the solvent used for coating decreases. In addition, there may be the case where the polymer cannot be produced in a stable manner. The Mw is more preferably from 150,000 to 2,000,000, and most preferably from 200,000 to 1,500,000. Although the Mw can be determined by various known methods, a value determined by gel permeation chromatography (hereinafter abbreviated to GPC) using polymethyl methacrylate as a standard was used in the present invention.

The polymer may be either a random copolymer or a block copolymer. The random copolymer is, however, more preferable since the block copolymer may have a tendency of decreasing the solubility in a solvent when used for coating and may have a tendency of impairing coating uniformity due to micelle formation in the solution. As the form of the polymer molecule chain, a linear polymer is more preferable since a branched polymer may have a tendency of decreasing the solubility in a solvent when used for coating and may have a tendency of impairing coating uniformity due to micelle formation in the solution.

The polymer of the present invention is preferably a nonionic-type polymer. The term "nonionic" refers to the properties of the polymer neither anionized nor cationized by blood or body fluid around the neutral pH, and containing neither a negatively charged functional group such as a carboxylic acid group, sulfonic group, phosphate group, and phenol group nor a positively charged functional group such as a primary amino group, secondary amino group, tertiary amino group, quaternary ammonium group, pyridyl group, and imidazoyl group in the molecule.

The blood clotting factor XII is said to be activated and cause a chain reaction in the clotting system on a negatively charged material surface. A positively charged material surface, on the other hand, tends to adsorb blood cells such as erythrocytes, platelets, and leukocytes due to the electrostatic interaction with the negative charge on the cell surface. JP-A 06-51060 discloses a technology for removing leukocytes more efficiently while preventing platelet adsorption by providing a slightly positively charged surface. However, electrostatic interaction is not desirable, because high platelet recovery performance is necessary for processing a large amount of blood. When the polymer is nonionic, the clotting system is activated only slightly so that stable platelet recovery performance can be attained even if the polymer is used for large scale blood treatment such as extracorporeal circulation.

A common polymerization method can be employed for synthesizing the polymer of the present invention. Addition polymerization (vinyl polymerization) and the like involving chain reactions; isomerization polymerization; and dissociation reaction, polyaddition, polycondensation, addition polycondensation, and the like involving consecutive reactions may be employed. Radicals, ions, and the like can be used as chain carriers in producing the polymer.

As the type of polymerization, solution polymerization, mass polymerization, deposition polymerization, emulsion polymerization, and the like can be given. Of these, solution polymerization is preferable. An example of the polymerization method is given below. An ethanol solution in which each monomer or a diazo initiator is dissolved is added dropwise to ethanol used as a polymerization solvent while stirring at a constant temperature below the boiling point of ethanol in a nitrogen atmosphere. A stabilizer and the like may be added as appropriate. The reaction yield is measured and confirmed by using a known method such as gas chromatography.

The reaction product may be purified by a common chemical purification method to remove impurities such as low molecular weight components and unreacted materials which are contained in the polymer or the reaction solution containing the polymer. As the purification method, a method comprising dissolving the reaction mixture in a solvent that dissolves the impurities, but does not dissolve the polymer, to cause the polymer to precipitate, and separating the precipitate (polymer) by filtration, decantation, or the like can be given. As required, the precipitate is washed with a solvent with solubility slightly higher than that of the precipitation solvent (a mixture of the precipitation solvent and a solvent, for example) and the precipitate is dried under reduced pressure until the weight of the precipitate becomes constant, thereby obtaining a solid polymer.

The polymer of the present invention can be suitably used for the surfaces of medical maetrials, because the polymer can increase the biocompatibility of a medical material when coated on the surface. For example, the polymer can be used for artificial organs such as an artificial blood vessel, artificial kidney, and artificial liver, blood cell separation filters such as a leukocyte removal filter, dialysis membrane, anti-thrombus material, and the like. In particular, since the polymer can selectively remove leukocytes from blood, that is, a concentrated erythrocyte preparation, concentrated platelet preparation, platelet poor plasma preparation, peripheral blood, cell floating solutions containing leukocytes and platelets such as lymph and marrow fluid, the polymer can be suitably used as a selective leukocyte removal filter of blood preparations and a selective leukocyte removing filter for extracorporeal circulation. In addition, since the polymer is eluted only with difficulty and is stable even if caused to be in contact with an aqueous solution for a long period of time, the polymer can be most suitably used for selective leukocyte removal apparatus for extracorporeal circulation designed to process a large amount of blood.

The present invention also provides a filter material for selective removal of leukocytes characterized by having the biocompatible polymer of the present invention present at least on the surface of the filter supporting body. The term "having the polymer present at least on the surface of the supporting material" indicates the polymer is present on the surface of the supporting material substantially covering the surface. As the method for having the polymer present on the surface of filter, known methods such as a method of coating or depositing and insolubilizing the polymer on the supporting body of the filter, a method of phase-separating the polymer from the supporting body of the filter during fabrication, and the like can be used. Of these, the method of coating is most preferable due to the easy industrial applicability and excellent performance stability.

Since the polymer used for the filter material for selectively removing leukocytes of the present invention comes into contact with body fluids such as blood, it is desirable that the polymer has extremely low solubility in water. To prevent detachment of the polymer from the filter supporting material, it is desirable that the polymer has high adsorption with filter supporting material. As the index for solubility of the polymer in water and adsorption of the polymer with the filter supporting body, the δ-value of the solubility parameter described in J. H. Hildebrand and R. L. Scott, *The Solubility of Nonelectrolytes*, 3rd ed. (Dover Pub., New York) can be used. In general, the closer the δ-value of two substances, the stronger the adsorption and the higher the solubility of the two substances. Therefore, the polymer used for the filter material for selectively removing leukocytes of the present invention should preferably have a δ-value that differs largely from the δ-value (23.3) of water and is close to the δ-value of the filter supporting body. A combination of the polymer having a δ-value in the range from 10.0 to 11.5 and the filter supporting body having the δ-value of in the range from 7.0 to 15.0 can produce a filter material with extremely low solubility in water without a risk of detachment of the polymer from the filter supporting body. A more preferable combination is the polymer's δ-value of 10.0 to 10.8 and the filter supporting body's δ-value of 7.2 to 14.5, and a still more preferable combination is the polymer's δ-value of 10.0 to 10.5 and the filter supporting body's δ-value of 7.5 to 14.0.

The δ-values can be calculated according to the following formula (1) which is described in the above document:

$$\delta = (E/V)^{1/2} \tag{1}$$

wherein E is cohesive energy (cal mol$^{-1}$) and V is molar volume (cm$^3$ mol$^{-1}$).

*The Adhesion Handbook*, Second Edition, edited by The Adhesion Society of Japan (THE NIKKAN KOGYO SHIMBUN, LTD.) describes δ-values of solvents and polymers measured heretofore. These values can be used. When the values E and V in the formula (1) are unknown, the δ-values can be calculated from the molecular structure according to the Fedors method described in Kozo Shinoda, Solution and Solubility, Maruzen Co., Ltd. Using the Fedors method, the e (cohesive energy (cal mol$^{-1}$)) values and the v (molar volume (cm$^3$ mol$^{-1}$)) values that have been calculated by the Fedors for various structural units of compounds are integrated to determine the E value and V value of the compound. The δ-value of the compound is then calculated using the E value and V value. The resulting δ-value is very close to the measured value.

Any material having a δ-value of the above range and not damaging blood cells can be used as the filter supporting body for the filter material for selectively removing leukocytes of the present invention without specific limitations. As examples of such a material, polyester, polyolefin, polyacrylonitrile, polyamide, polystyrene, polyalkyl (meth)acrylate, polyvinyl chloride, polychloroprene, polyurethane, polyvinyl alcohol, polyvinyl acetate, polysulfone, polyether sulfone, polybutadiene, butadiene-acrylonitrile copolymer, styrene-butadiene copolymer, ethylene-vinyl alcohol copolymer, cellulose diacetate, and ethyl cellulose can be given. Of these, polyester and polyolefin are preferable, with a particularly preferable organic filter material being polyester.

Various methods can be used for coating the polymer onto the filter supporting body without any specific limitations inasmuch as the surface of the filter supporting body can be coated with a certain degree of uniformity without unduly clogging the pores in the filter supporting body. Examples of the method for coating the polymer onto the filter supporting body include, but are not limited to, a method of impregnating the filter supporting body with a polymer solution, a method of spraying the polymer solution to the filter supporting body, and a method of applying or transcribing the polymer solution to the filter supporting body using a rotogravure roll or the like. Of these methods, the method of impregnating the filter supporting body with a polymer solution and the method of applying or transcribing the polymer solution to the filter supporting body using a rotogravure roll are preferable due to the excellent continuous productivity and low cost.

Various solvents that do not dissolve the filter supporting body to a noticeable degree can be used as the solvent to dissolve the polymer in the coating operation without any specific limitations. Examples of such a solvent include, but are not limited to, water and aqueous solutions containing an inorganic salt, alcohols such as methanol, ethanol, propanol, and butanol, ketones such as acetone and methyl ethyl ketone, esters such as methyl acetate and ethyl acetate, hydrocarbons such as benzene and cyclohexane, halogenated hydrocarbons such as chloroform and dichloromethane, sulfur-containing solvents such as dimethyl sulfoxide, amides such as dimethylformamide and dimethylacetamide, and mixtures of two or more of the above solvents to the extent possible.

The concentration of the polymer solution used for coating is preferably 0.001 wt % or more, but less than 10 wt %. If the concentration is less than 0.001 wt %, the amount of the polymer on the surface is too small for the filter material to exhibit sufficient biocompatibility such as properties of preventing platelet adsorption. If the concentration is 10 wt % or more, on the other hand, not only does the solution have too great a viscosity to be handled with ease, but also the surface properties of the medical material may be significantly affected. In addition, such a high concentration is too expensive to be efficiently used. For these reasons, the polymer concentration is more preferably 0.005 wt % or more, but less than 7 wt %, and most preferably 0.01 wt % or more, but less than 5 wt %. The amount of the polymer held on the filter supporting material is preferably 0.001 wt % or more, but less than 10 wt %. If less than 0.001 wt %, the amount of the polymer on the surface is too small for the filter material to exhibit sufficient biocompatibility such as properties of preventing platelet adsorption. If 10 wt % or more, the amount of the polymer is excessive, giving rise to easy elution of the polymer when the filter material comes into contact with an aqueous solution such as blood. A more preferable amount of the polymer is 0.005 wt % or more, but less than 7 wt %, with the amount of 0.01 wt % or more, but less than 5 wt % being most preferable.

To dry the polymer solution after coating, a method comprising removing excess solvent by mechanical compression, by gravity, or by injecting gas such as air or nitrogen, and treating the coated material in dry air or under reduced pressure at atmospheric temperature or with heating can be employed. Adsorption of the polymer to the filter supporting body may be further increased by a heat treatment after coating the polymer or by post processing of irradiating the coated surface with γ-rays, electron beams, or the like. The coating operation may be carried out either during manufacturing the filter supporting body or after manufacturing the filter supporting body.

The polymer coating rate in the entire surface of the leukocyte removal filter material of the present invention is preferably from 40% to 90%. The coating rate in the present invention refers to the proportion of the area covered with the polymer in the entire surface area of the filter supporting body. If the coating rate is less than 40 wt %, the amount of the polymer on the surface is too small for the filter material to exhibit sufficient biocompatibility such as properties of rejecting platelet adsorption. If 90 wt % or more, the amount of the polymer is excessive, giving rise to easy elution of the polymer when the filter material comes into contact with an aqueous solution such as blood. A more preferable range of coating rate is from 45% to 85%, with a still more preferable range being from 50% to 80%.

The coating rate can be determined using an analyzer commonly used to analyze polarized surfaces such as an XPS (X-ray Photoelectron Spectroscopy) analyzer or a TOF-SIMS (Time Of Flight-Secondary Ion Mass Spectrometry) analyzer. When two or more analytical methods can be used for measuring the surface coating rate, the value obtained using the XPS and the like in which method the information at the depth from several tens to one hundred Å (angstrom) from the surface is deemed to be correct, but when the surface properties permits only measurement of the coating rate by the SIMS method or the like, the value obtained using one of these methods is regarded to be correct.

The method of measuring the coating rate will now be described in more detail by way of a specific example.

In the case of a filter material prepared by coating a filter supporting body of polyethylene terephthalate nonwoven fabric with a polymer made from three polymerizable monomers (methoxydiethylene glycol methacrylate, methyl methacrylate, and 2-hydroxyisobutyl methacrylate), the coating rate can be determined as follows.

C1s spectra of the filter material coated with the polymer, the filter supporting body, and the polymer are measured using an XPS analyzer. The height ratio of the peak (286 eV) originating from the —C—O— component and the peak (289 eV) originating from the —C—O—O— component in the C1s spectrum is determined. The height ratio herein refers to the value calculated by dividing the height of the peak originating from the —C—O— component by the height of the peak originating from the —C—O—O— component. In the case of polyethylene terephthalate, since the molecular structure does not have the —C—O— component other than that originating from the —C—O—O— component, the height of the peak originating from the —C—O— component is equivalent to the height of the peak originating from the —C—O—O— component. Therefore, the height ratio of polyethylene terephthalate is 1. Because the above polymer contains the —C—O— component other than that originating from the —C—O—O— component, the height ratio increases in proportion to the content of the polymer. The coating rate can be determined using the following formula.

Coating rate=$(A-B)/(C-B)$ wherein A is the height ratio of the filter material coated with the polymer, B is the height ratio of the filter supporting body, and C is the height ratio of the polymer.

To increase contact with blood in a liquid phase, it is desirable for the filter material for selectively removing leukocytes of the present invention to have a configuration with a large surface area. For example, fibrous structural materials in the form of a nonwoven fabric, fiber, cotton, yarn, bundle, screen, and fabric; polymer porous materials such as sponge; and other structural materials in the form of beads, gel, and the like can be given. Fabric and nonwoven fabric are particularly preferable in view of adsorptivity of leukocytes and handling easiness as a separating medium. Nonwoven fabric is most preferable due to the capability of providing many contact points with leukocytes.

In the case of a fibrous structural material such as nonwoven fabric, the average fiber diameter, which affects the cell adsorption capability, is important. If the fiber diameter is too large, the amount and rate of adsorption of leukocytes decrease; if too small, the amount of platelet adsorption increases. The average fiber diameter of the filter material of the present invention is preferably from 0.5 μm to 50 m, and more preferably from 1 μm to 40 μm, and most preferably from 2 μm to 35 μm.

The average fiber diameter in the present invention is determined as follows. A portion deemed to be substantially homogeneous is sampled from one or more pieces of fabrics forming the filter material and photographed using a scanning electron microscope or the like. For sampling, an effective filtration cross-sectional area of the fabric is divided into squares with one side length of 0.5 cm and six squares are randomly sampled. In random sampling, each divided square is numbered and the required number of squares is selected by using a table of random numbers, for example. Photographs with a magnification of 2,500 are taken at three or more, preferably five or more locations for each sampled square. Photographs for the central parts and the neighborhood areas of each sampled square are taken until the total number of fibers taken in the photographs becomes 100. The diameter herein refers to the width of fiber in the direction perpendicular to the fiber axis. Then, the average diameter is determined by dividing the sum of the diameters of all measured fibers by the number of the fibers. However, the data obtained are excluded, for example, in the cases where multiple fibers overlap precluding diameter measurement of a fiber which hides itself behind another fiber, multiple fibers are consolidated into a fiber with a larger diameter due to fusing or else, or there are fibers with remarkably different diameters.

The present invention also provides a filter apparatus for selective removal of leukocytes characterized by having the filter material of the present invention filled in a container having at least an inlet port and an outlet port. There are no specific limitations to the shape of the container inasmuch as the container has an inlet port and an outlet port. Examples of such a container include a container in which the filter material for selectively removing leukocytes can be filled in the form of laminated layers, a cylindrical container, a columnar container such as a triangular prism, a quadratic prism, a hexagonal cylinder, and octagonal cylinder, a container in which the filter material for selectively removing leukocytes rolled in the form of a cylinder can be filled, and a cylindrical container allowing a blood flow to come into the cylinder from the outer perimeter, converging blood into the innermost area, and letting the blood to flow out from an outlet port. Furthermore, a container in which the cross-sectional area decreases from the inlet port toward the outlet port is preferably used.

The filling density of the filter material for selectively removing leukocytes in the container of the present invention, which refers to the weight of the packed filter material per unit volume of the container, is from 0.05 $g/cm^3$ to 0.5 $g/cm^3$. To increase the efficiency of selective removal of leukocytes, while ensuring a smooth flow of blood by preventing clogging of the filter and suppressing a pressure loss increase, the filling density is preferably from 0.075 $g/cm^3$ to 0.4 $g/cm^3$, and most preferably from 0.1 $g/cm^3$ to 0.35 $g/cm^3$.

Figure 1:
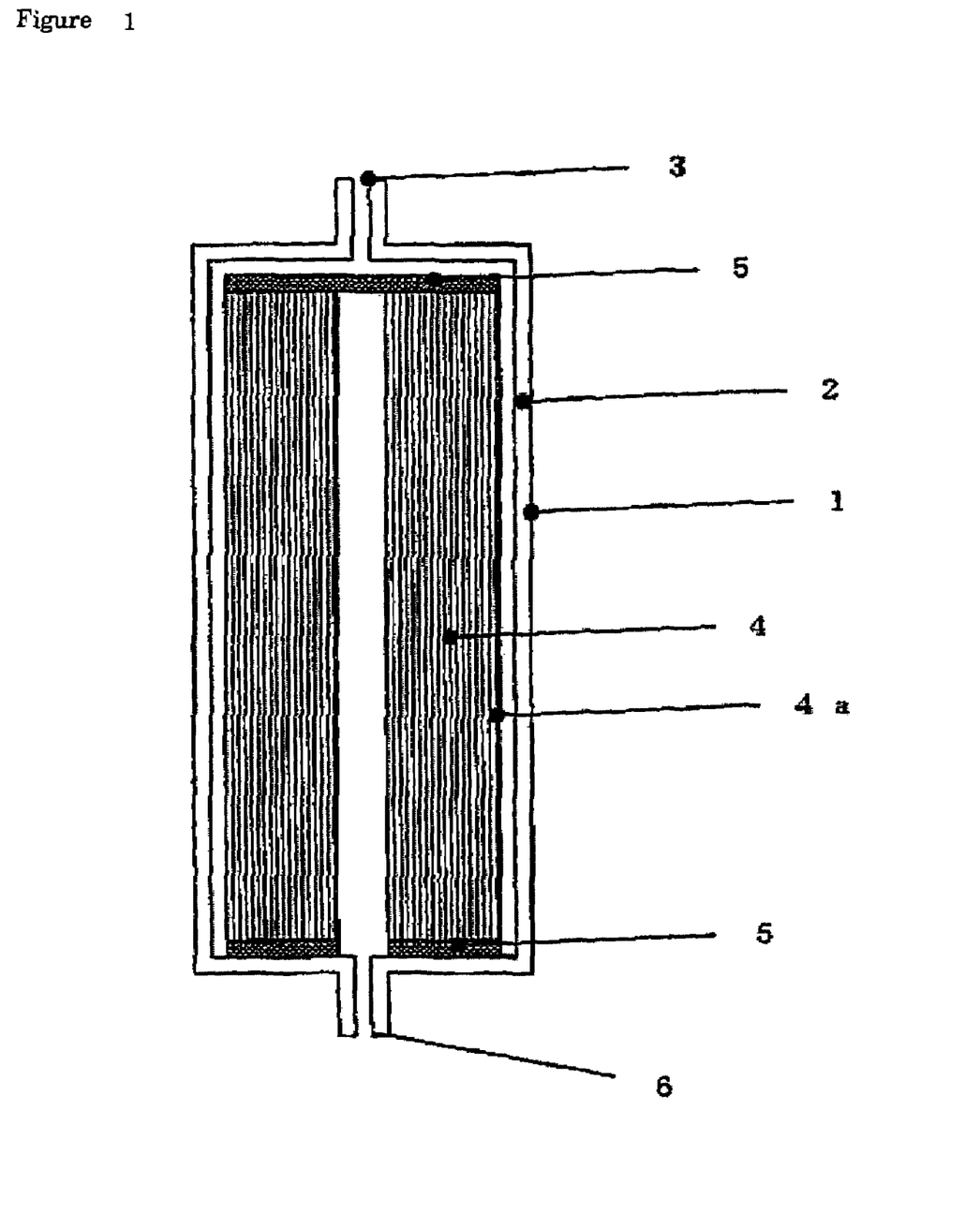
FIG. 1 is a cross-sectional view of the leukocyte-removal filter apparatus of the present invention.

An embodiment of the filter apparatus for selectively removing leukocytes of the present invention will now be specifically described below using the drawings. FIG. 1 is a cross-sectional view of one embodiment of the filter apparatus for selectively removing leukocytes of the present invention.

In a preferred embodiment of the filter apparatus (1) for selectively removing leukocytes of the present invention, the filter material for selectively removing leukocytes is rolled in the form of a cylinder to provide a hollow cylindrical filter (4), which is packed in a cylindrical container (2) with the both ends (5, 5) being sealed liquid-tight so as not to allow blood to flow. A sealing material with excellent compatibility with blood when caused to come in contact with blood and possessing liquid-tight properties is used. Known synthetic resins such as urethane can be used. A blood inlet port (3) may be provided at any optional location of the container which allows the blood to be processed to be supplied to the outer or inner perimeter of the hollow cylindrical filter of which the both ends are sealed. A blood outlet port (6) may be provided in any location communicated with the inner perimeter when the blood to be processed is supplied to the outer perimeter or any location communicated with the outer perimeter when the blood to be processed is supplied to the inner perimeter.

The hollow cylindrical filter in the filter apparatus for selective removal of leukocytes of the present invention preferably has a filtration area of the first blood contact layer (4a) from 50 $cm^2$ to 1,000 $cm^2$. The first blood contact layer in the present invention refers to a part of the hollow cylindrical filter with which the blood to be processed supplied from the inlet port comes into contact for the first time. The first blood contact layer may be any part of the outer or inner perimeter of the hollow cylindrical filter. Platelets are said to abundantly bond with the von Willebrand factor through GPIIb/IIIa acceptor under a high shearing stress and to undergo activated clotting. Therefore, to increase the platelet recovery rate, it is desirable to cause the blood to come into contact with the first contact layer moderately at a low flow rate. If the filtration area of the first blood contact layer is less than 50 $cm^2$, the blood flow rate per unit filtration area increases, resulting in a reduction in the platelet recovery rate. If the filtration area of the first blood contact layer is more than 1,000 $cm^2$, a large container is required for the filter apparatus. The filtration area is more preferably from 80 cm² to 500 cm², and still more preferably from 100 cm² to 400 cm².

To specify the volume standard specific surface area of the first blood contact layer in an appropriate range is preferable from the viewpoint of preventing the shearing stress given to platelets. The volume standard specific surface area as used in the present invention refers to the surface area per unit volume of the filter material and can be measured by a known method such as the BET method or the Langmuir method. When the filter material is fiber, the volume standard specific surface area can be calculated using the average fiber diameter, the specific gravity of fiber, and the like. The hollow cylindrical filter in the filter apparatus for removing leukocytes of the present invention preferably has a volume standard specific surface area of the first blood contact layer in a range from 0.08 m²/ml to 1.0 m²/ml. The volume standard specific surface area is more preferably from 0.1 m²/ml to 0.8 m²/ml, and still more from 0.2 m²/ml to 0.5 m²/ml.

The hollow cylindrical filter in the filter apparatus for removing leukocytes of the present invention may be a scroll of a laminated body made of a filter material and a spacer layer material both in the form of a sheet. The term "spacer layer" in the present invention refers to a layer of a material in which blood can flow more easily than in the filter material for selectively removing leukocytes. A coarse mesh of metal, synthetic resin, inorganic fiber, or synthetic fiber, nonwoven fabric with an average fiber diameter larger than the nonwoven fabric used for the hollow cylindrical filter, and the like can be used as the spacer layer material. The spacer layer is laminated with the filter material for selectively removing leukocytes and rolled in the form of a scroll of cloth to secure the area that permits blood to easily flow between the hollow cylindrical filter. Both the starting and terminal ends of the spacer layer rolled in the form of a scroll are preferably open to the outer perimeter and/or the inner perimeter of the hollow cylindrical filter to provide a passage for blood.

The thickness of the hollow cylindrical filter in the leukocyte removal filter apparatus of the present invention is preferably from 0.6 mm to 12.0 mm. If the thickness is less than 0.6 mm, the filtration length is too small to provide blood components with sufficient opportunity to contact with the filter material, resulting in a poor leukocyte removal efficiency. If the thickness is more than 12.0 mm, the filtration length is so large that blood components are provided with too many opportunities to contact with the filter material, resulting in a decrease in the platelet recovery rate. A more preferable thickness range of the hollow cylindrical filter is from 1.0 mm to 10.0 mm, with a still more preferable thickness range being from 1.5 mm to 8.0 mm.

The hollow cylindrical filter in the filter apparatus for removing leukocytes of the present invention may be provided with a second blood contact layer on the downstream side of the first blood contact layer. Since the second blood contact layer has a function of removing leukocytes which have not been removed in the first blood contact layer, the second blood contact layer must have a volume standard specific surface area larger than that of the first blood contact layer. A preferable range of the volume standard specific surface area of the second blood contact layer is from 1.0 m²/ml to 20 m²/ml, and still more from 2.0 m²/ml to 15 m²/ml.

In addition, the thickness ratio of the laminated layers, that is, of the second blood contact layer to the first blood contact layer, is preferably from 0.2 to 10.0. The thickness ratio of the laminated layers in the present invention refers to the value obtained by dividing the thickness of the first blood contact layer by the thickness of the second blood contact layer. If the thickness ratio of the laminated layers is less than 0.2, the filtration length of the first blood contact layer is comparatively small. Therefore, the first blood contact layer cannot sufficiently mitigate the shearing stress which platelets receive in the second blood contact layer, giving rise to a decrease in the platelet recovery rate. The laminated layer thickness of more than 10.0 mm is undesirable because the volume of the first blood contact layer becomes large, so that a large container is required for the filter apparatus. For these reasons, the laminated layer thickness is more preferably from 0.3 to 8.0, and most preferably from 0.5 to 6.0.

The selective leukocyte removal filter apparatus of the present invention can be sterilized by a known method such as radiation sterilization, moist heat sterilization, chemical sterilization, gas sterilization, and dry heat sterilization. Moist sterilization by maintaining the filter material under the condition of the saturated moisture content or more using a filling liquid is preferable due to the simple priming operation. A more preferable method is radiation sterilization comprising irradiating the filter material with radiation such as γ-ray and electron beams or moist heat sterilization using high pressure steam or the like. Although any liquid not causing deterioration of the polymer can be used as the filling liquid, water or an aqueous solution of a water soluble substance having a minimal risk of damage to living bodies is preferable.

As the water-soluble substance having a minimal risk of damage to living bodies, compounds soluble in water exhibiting only a slight damage to living bodies, for example, salts such as sodium chloride, sodium carbonate, sodium hydrogencarbonate, sodium phosphate, sodium hydrogenphosphate, and sodium pyrosulfite, and water-soluble organic compounds such as glycerol, sodium citrate, gelatin, and casein can be given. A compound which may be harmful to living bodies if present in a large amount can also be used, if such a compound can be washed out from the blood cell separating filter by a simple washing procedure such as a priming operation to an extent that only a small amount not harmful to the living body remains after washing. A compound which can easily form an isotonic solution when dissolved in water may be very preferably used. These compounds can be used either individually or in combination of two or more. Preferable water-soluble compounds are sodium chloride, sodium carbonate, sodium hydrogencarbonate, sodium phosphate, sodium hydrogenphosphate, and sodium pyrosulfite, with sodium chloride being most preferable.

The condition of the saturated moisture content or more used herein may include a condition in which the filter material is entirely immersed in water of an aqueous solution of water soluble compound having a minimal risk to living bodies or a condition in which the filter material is sufficiently humidified in advance to become moistened to the saturated moisture content or more of the material. In short, it is sufficient for the filter material to be exposed to moisture in the amount equivalent to or more of the saturated moisture content of the filter material irrespective of the degree of exposure.

The concentration of the aqueous solution is preferably 5.0 wt % or less. If the concentration exceeds 5.0 wt %, it is difficult to remove the water-soluble substance by the priming operation. Since elution of the polymer can be prevented at a higher more certainty at a concentration of 0.01 wt % or more, a more preferable concentration range is from 0.01 wt % to 4.0 wt %, with a still more preferable concentration being from 0.1 wt % to 3.0 wt %.

The present invention also provides a system for selective removal of leukocytes comprising a blood delivery means, an anticoagulant fluid injection means, and a selective leukocyte removal means which contains the selective leukocyte removal filter apparatus of the present invention. The system for selective removal of leukocytes of the present invention can maintain stable selective leukocyte removal capability while preventing platelet adsorption even if a large amount of blood (e.g. 1-10 l) is processed.

Any known liquid delivery means such as a pump can be used as the blood delivery means. As the type of the pump, an inner-tube roller pump, a finger pump, and the like can be given. A pump that can accurately deliver the blood in a flow rate range from 5 ml/min to 500 ml/min is particularly preferable in the present invention.

The blood flow rate using the blood delivery means in the selective leukocyte removal system of the present invention is preferably from 10 ml/min to 200 ml/min. If the blood flow rate is less than 10 ml/min, the blood tends to stagnate in the selective leukocyte removal filter apparatus. If the flow rate is greater than 200 ml/min, the shearing stress significantly increases, resulting in a decrease of the platelet recovery rate. For these reasons, the blood flow rate is more preferably from 15 ml/min to 150 ml/min, and most preferably from 20 ml/min to 100 ml/min.

The anticoagulant fluid injection means used in the present invention preferably has a capacity of feeding the anticoagulant fluid to the blood flow circuit at a flow rate from 1% to 20% of the blood flow rate. The anticoagulant may be charged either as is or after dilution. If the flow rate is less than 1% of the blood flow rate, it is difficult for the anticoagulant to mix with the blood and, therefore, to exhibit a sufficient anticoagulation effect. The flow rate of the anticoagulant more than 20% of the blood flow rate is not desirable in practice, because the blood may be excessively diluted. For these reasons, the flow rate of the anticoagulant fluid is more preferably from 3% to 18%, and most preferably from 5% to 18% of the blood flow rate.

As the type of the anticoagulant contained in the anticoagulant fluid used in the present invention, heparins such as heparin sodium, heparin calcium, and dalteparin sodium; protease inhibitors such as nafamostat mesilate and gabexate mesilate; and citric acid-based anticoagulants such as ACD-A, ACD-B, and CPD; and the like can be preferably used. The above anticoagulants can be used more efficiently, when diluted with a buffer solution such as a physiological saline solution or a glucose solution which neither affects the anticoagulation effect nor denatures blood constituents.

In the case of heparin or a low molecular weight heparin, for example, the amount of the anticoagulant added to 1 l of blood is from 100 to 2,000 units, and preferably from 300 to 1,500 units. In the case of nafamostat mesilate, the amount is from 2 to 40 mg, and preferably from 6 to 30 mg. In the case of ACD-A or ACD-B solution, the effective anticoagulant amount is from 20 to 160 ml, and preferably from 30 to 125 ml.

As the means for adding an anticoagulant solution, any means typified by commonly used metering pumps such as a roller inner tube pump, finger pump, infusion pump, and syringe pump can be used. More specifically, an inner tube roller pump, a finger pump, and the like by which a very small quantity of a fluid can be injected at a high precision can be suitably used.

The selective leukocyte removal system of the present invention can be constructed by liquid-tight joining of the above-described blood delivery means, anticoagulant fluid injection means, and selective leukocyte removal means using a blood circuit to introduce blood to the selective leukocyte removal means and a blood circuit to discharge the blood from the selective leukocyte removal means, thereby forming a circuit for extracorporeal circulation. To form the entire configuration, the blood delivery means and the anticoagulant fluid injection means are provided in the circuit on the blood introduction side having a blood recovering means, for example, and this circuit is joined to the blood inlet port side of the selective leukocyte removal means. The system can be preferably used for extracorporeal circulation if the blood discharge side circuit having a means for returning blood to the patient is provided on the blood exit side of the selective leukocyte removal means.

Figure 2:
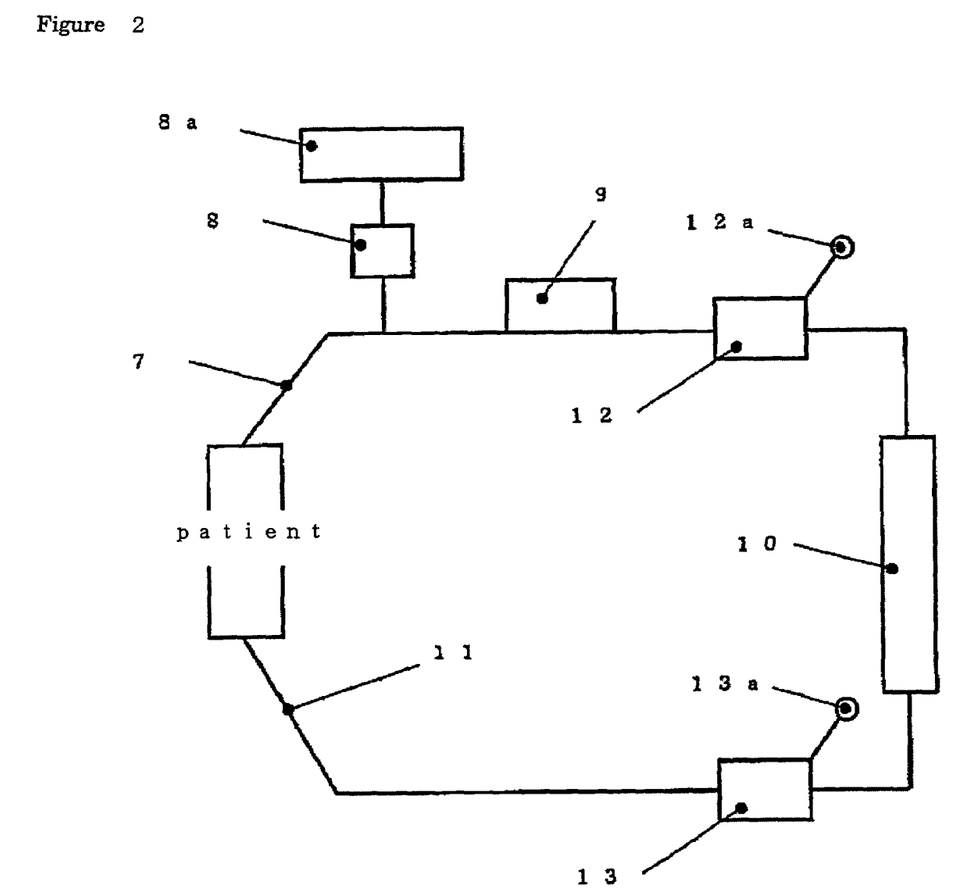
FIG. 2 is a schematic drawing showing one embodiment of the system for selective leukocyte removal of the present invention.

FIG. 2 is a schematic diagram showing one embodiment of the selective leukocyte removal system of the present invention. In the selective leukocyte removal system of FIG. 1, the system comprises a means (7) to extract blood from a patient, an anticoagulant fluid injection means (8) to inject an anticoagulant fluid (8a) into the extracted blood, a blood delivery means (9) to deliver the blood mixed with the anticoagulant at a flow rate of 10-200 ml/min, a micro aggregate capture means (12) having an arterial pressure monitor (12a) and a selective leukocyte removal filter apparatus. A selective leukocyte removal means (10) having an inlet port and a blood outlet port, a drip chamber (13) having a venous pressure monitor (13a), and a means (11) to return the blood to the patient are liquid tightly connected in that order.

The present invention also provides a method of using the selective leukocyte removal filter material for treating cellular immune abnormality, comprising causing the blood of a patient suffering from the cellular immune abnormality to come in contact with the filter of the present invention. To complete the medical treatment of the disease using the method of the present invention, the blood after processing may be returned to the patient. This can be preferably carried out by applying various means and methods of use described in connection with the selective leukocyte removal system. The cellular immune abnormality as used in the present invention refers to a disease in which immunocompetent cells, cytotoxic-T cells, inflammatory cells, and the like in the living body present abnormalities to produce an inflammation inducing substance such as cytokine, by which the body tissues are attacked. Autoimmune diseases such as or malignant rheumatoid arthritis, systemic erythematodes, Behcet's disease, idiopathic thrombo cytopenic purpura, and autoimmune hepatitis; inflammatory bowel diseases such as ulcerative colitis and Crohn's disease; allergic diseases such as atopic dermatitis; rapidly progressive glomerulonephritis; and systemic inflammatory response syndrome are given as examples.

It is desirable that the selective leukocyte removal system of the present invention has leukocyte removal capability in terms of the leukocyte removal rate of 50% or more. The leukocyte removal rate can be determined in the present invention from the leukocyte concentration in the blood on the inlet port side introduced into the selective leukocyte removal means and the leukocyte concentration in the blood on the outlet port side discharged from the selective leukocyte removal means according to the following formula.

Leukocyte removal rate (%)=(1−Leukocyte concentration on the outlet port side/Leukocyte concentration on the inlet port side)×100

If the leukocyte removal rate is less than 50%, the amount of leukocytes removed in one process is not sufficient, only giving a limited improvement effect on the cellular immune abnormality. A more preferable leukocyte removal rate is 60% or more, with a 70% or more leukocyte removal rate being most preferable.

In regard to the platelet recovery capability, it is desirable that the platelet recovery rate is 50% or more. The platelet recovery rate can be determined in the present invention from the platelet concentration in the blood on the inlet port side introduced into the selective leukocyte removal means and the platelet concentration in the blood on the outlet port side discharged from the selective leukocyte removal means according to the following formula.

Platelet recovery rate (%)=(Platelet concentration on the outlet port side/Platelet concentration on the inlet port side)×100

If the platelet recovery rate is less than 50%, the amount of platelet recovered may be too small when processing blood containing a small amount of platelets (e.g. 100,000 platelets/μl or less). A more preferable platelet recovery rate is 60% or more, with a 70% or more platelet recovery rate being most preferable.

EXAMPLES

The present invention is described below by examples, which should not be construed as limiting the present invention.

Example 1

(Synthesis of Polymer)

One example of the method of synthesizing the polymer used for preparing a selective leukocyte removal filter by coating will be shown. A reaction vessel equipped with a reflux condenser was charged with ethanol (277 ml). After bubbling nitrogen into ethanol and stirring the mixture at 73° C. for one hour, monomers were added dropwise over 120 minutes while maintaining a nitrogen atmosphere. An initiator solution was added dropwise at the same time over 300 minutes. After completion of the addition of the initiator solution, the monomers were polymerized for further two hours.

The monomer mixture was a liquid containing 4.8 g (30.0 mmol) of methoxydiethylene glycol methacrylate (MDG), which is a polymerizable monomer having an alkylene oxide chain, 4.3 g (50.0 mmol) of methylmethacrylate (MMA), which is a polymerizable monomer having a hydrophobic group, and 2.7 g (20.0 mmol) of 2-hydroxyisobutyl methacrylate (HBMA), which is a polymerizable monomer having a hydroxyl group. The molar ratio of the monomers was 30 mol % (MDG): 50 mol % (MMA): 20 mol % (HBMA). An ethanol solution containing 0.034 g of azobisdimethylvaleronitrile (V-65) was used as the initiator solution. The reaction mixture was added dropwise to purified water to cause the polymer to precipitate. The recovered polymer precipitate was cut into pieces and once again put into purified water, followed by stirring for one hour to wash the polymer. Next, the washed polymer was dried under vacuum at 60° C. to obtain the target polymer.

The composition of the resulting polymer was analyzed from the integral value of NMR measurement, confirming that the composition was almost in agreement with the charged monomer composition. The δ value of the polymer was calculated according to the Fedors method to confirm that the δ value was 10.29. The weight average molecular weight of the polymer measured by GPC was $6.8 \times 10^5$.

(Preparation of Filter Material)

Next, a method of preparing the filter material for selectively removing leukocytes will be described. 1 g of the polymer obtained was dissolved in 100 ml of a mixed solvent of ethanol and purified water (70:30). A nonwoven fabric made from polyethylene terephthalate was immersed in the solvent. After removing excessive liquid, the nonwoven fabric was dried at room temperature for 16 hours to obtain the target filter. The δ value of the filter supporting body was 10.30, the average fiber diameter of the filter material was 2.7 μm, the density was 90 g/m², and the thickness was 0.42 mm.

(Elution Test)

The method of the elution test was as follows. A 200 ml container was packed with 15 g of the filter material prepared in the above, a physiological saline solution was filled into the container, and the content was sterilized with γ-ray (irradiation dose: 25 kGy). To confirm elution in the temperature range possibly occurring during actual preservation of medical devices, the container was allowed to stand at 25° C. for 24 hours, then at 4° C. for 24 hours. The appearance of the filled solution after preservation was observed to confirm that the solution was transparent and colorless, with no change as compared with the state before sterilization. The maximum absorbance of the filled solution was measured using an ultraviolet spectrophotometer (V-560, manufactured by JASCO Corp.) at a wavelength of 220 nm to 350 nm to find that the maximum absorbance was 0.04.

(Evaluation of Blood Properties)

Next, a test method for evaluating the leukocyte removal rate and platelet recovery rate will be described. The filter material prepared in the above was cut into disks, each with a diameter of 6.8 mm. Seven sheets of the disks were laminated in a 1 ml column having an inlet port and an outlet port. The column was filled with a physiological saline solution and sterilized with γ-ray (irradiation dose: 25 kGy) to prepare the column for performance evaluation. 3 ml of fresh human blood (number of leukocytes: 4,500-8,400/μl, number of platelets: 150,000-440,000/μl) to which ACD-A was added as an anti-coagulator (blood:ACD-A=8:1) was fed into the column from the inlet port using a syringe pump at a constant flow rate of 0.5 ml/min. The processed blood was recovered. The leukocyte concentration and platelet concentration in the blood before and after passing through the column were measured using an automatic blood cell counter (Sysmex SF-3000, manufactured by To a Medical Electronics Co., Ltd.), and the leukocyte removal rate and the platelet recovery rate were calculated.

As a result, the leukocyte removal rate was 97.5% and the platelet recovery rate was 85.0%, confirming selective leukocyte removal capability.

Example 2

A polymer was synthesized in the same manner as in Example 1, except for using 40.0 mol % of MDG, 50.0 mol % of MMA, and 10 mol % of HBMA. The composition of the resulting polymer was analyzed from the integral value of NMR measurement, confirming that the composition was almost in agreement with the charged monomer composition. The γ value of the polymer was calculated according to the Fedors method to confirm that the γ value was 10.04. The weight average molecular weight of the polymer measured by GPC was $8.7 \times 10^5$.

A filter material was prepared from the polymer in the same manner as in Example 1. The δ value of the filter supporting body was 10.30, the average fiber diameter of the filter material was 2.7 μm, the density was 90 g/m², and the thickness was 0.42 mm.

Using the obtained filter material, the elution test and the blood performance test were carried out in the same manner as in Example 1. The appearance of the filled solution after sterilization and preservation confirmed that the solution was transparent and colorless, with no change as compared with the state before sterilization. The maximum absorbance of the filled solution was measured using an ultraviolet spectrophotometer at a wavelength of 220 nm to 350 nm to find that the maximum absorbance was 0.05. The leukocyte removal rate was 97.0% and the platelet recovery rate was 85.0%, confirming selective leukocyte removal capability.

Example 3

A polymer was synthesized in the same manner as in Example 1, except for using 20 mol % of MDG, 60 mol % of MMA, and 20 mol % of HBMA. The composition of the resulting polymer was analyzed from the integral value of NMR measurement, confirming that the composition was almost in agreement with the charged monomer composition. The δ value of the polymer was calculated according to the Fedors method to confirm that the δ value was 10.31. The weight average molecular weight of the polymer measured by GPC was $9.2 \times 10^5$.

1 g of the polymer obtained was dissolved in 100 ml of a mixed solvent of ethanol and purified water (70:30). A nonwoven fabric made from polypropylene was immersed in the solvent. After removing excessive liquid, the nonwoven fabric was dried at room temperature for 16 hours to obtain the target filter. The δ value of the filter supporting body was 7.90, the average fiber diameter of the filter material was 2.6 μm, the density was 80 g/m$^2$, and the thickness was 0.51 mm.

Using the obtained filter material, the elution test and the blood performance test were carried out in the same manner as in Example 1. The appearance of the filled solution after sterilization and preservation confirmed that the solution was transparent and colorless, with no change as compared with the state before sterilization. The maximum absorbance of the filled solution was measured using an ultraviolet spectrophotometer at a wavelength of 220 nm to 350 nm to find that the maximum absorbance was 0.08. The leukocyte removal rate was 98.5% and the platelet recovery rate 89.4%, confirming selective leukocyte removal capability.

Example 4

A polymer was synthesized in the same manner as in Example 1, except for using n-butyl methacrylate (BMA) as a polymerizable monomer having a hydrophobic group and 2-hydroxyisopropyl methacrylate (HPMA) as a polymerizable monomer having a hydroxyl group, and charging 20 mol % of MDG, 50 mol % of BMA, and 30 mol % of HPMA. The composition of the resulting polymer was analyzed from the integral value of NMR measurement, confirming that the composition was almost in agreement with the charged monomer composition. The δ value of the polymer was calculated according to the Fedors method to confirm that the δ value was 10.46. The weight average molecular weight of the polymer measured by GPC was $1.1 \times 10^5$.

A filter material was prepared from the polymer in the same manner as in Example 1. The δ value of the filter supporting body was 10.30, the average fiber diameter of the filter material was 2.7 μm, the density was 90 g/m$^2$, and the thickness was 0.42 mm.

Using the obtained filter material, the elution test and the blood performance test were carried out in the same manner as in Example 1. The appearance of the filled solution after sterilization and preservation confirmed that the solution was transparent and colorless, with no change as compared with the state before sterilization. The maximum absorbance of the filled solution was measured using an ultraviolet spectrophotometer at a wavelength of 220 nm to 350 nm to find that the maximum absorbance was 0.08. The leukocyte removal rate was 93.8% and the platelet recovery rate was 83.7%, confirming selective leukocyte removal capability.

Example 5

A polymer was synthesized in the same manner as in Example 1, except for using 15 mol % of MDG, 40 mol % of MMA, and 45 mol % of HBMA. The composition of the resulting polymer was analyzed from the integral value of NMR measurement, confirming that the composition was almost in agreement with the charged monomer composition. The δ value of the polymer was calculated according to the Fedors method to confirm that the δ value was 10.86. The weight average molecular weight of the polymer measured by GPC was $2.1 \times 10^5$.

A filter material was prepared from the polymer in the same manner as in Example 1. The δ value of the filter supporting body was 10.30, the average fiber diameter of the filter material was 2.7 μm, the density was 90 g/m$^2$, and the thickness was 0.42 mm.

Using the obtained filter material, the elution test and the blood performance test were carried out in the same manner as in Example 1. The appearance of the filled solution after sterilization and preservation confirmed that the solution was transparent and colorless, with no change as compared with the state before sterilization. The maximum absorbance of the filled solution was measured using an ultraviolet spectrophotometer at a wavelength of 220 nm to 350 nm to find that the maximum absorbance was 0.15. The leukocyte removal rate was 82.2% and the platelet recovery rate was 80.2%, confirming selective leukocyte removal capability.

Comparative Example 1

A polymer was synthesized in the same manner as in Example 1, except for using 5.0 mol % of MDG, 5.0 mol % of MMA, and 90.0 mol % of HPMA. The composition of the resulting polymer was analyzed from the integral value of NMR measurement, confirming that the composition was almost in agreement with the charged monomer composition. The δ value of the polymer was calculated according to the Fedors method to confirm that the δ value was 12.39. The weight average molecular weight of the polymer measured by GPC was $3.2 \times 10^5$.

A filter material was prepared from the polymer in the same manner as in Example 1. The δ value of the filter supporting body was 10.30, the average fiber diameter of the filter material was 2.7 μm, the density was 90 g/m$^2$, and the thickness was 0.42 mm.

Using the obtained filter material, the elution test and the blood performance test were carried out in the same manner as in Example 1. The filled solution after sterilization and preservation was turbid, confirming that the polymer eluted during sterilization and preservation. The maximum absorbance of the filled solution was measured using an ultraviolet spectrophotometer at a wavelength of 220 nm to 350 nm to find that the maximum absorbance was 2.4. The leukocyte removal rate was 93.3% and the platelet recovery rate 3.1%, confirming a low platelet recovery rate.

Comparative Example 2

A polymer was synthesized in the same manner as in Example 1, except for using methoxynonaethylene glycol methacrylate (MNG) as a polymerizable monomer having a polyalkylene oxide chain and charging 65.0 mol % of MNG and 35.0 mol % of MMA. The composition of the resulting polymer was analyzed from the integral value of NMR measurement, confirming that the composition was almost in agreement with the charged monomer composition. The δ value of the polymer was calculated according to the Fedors method to confirm that the δ value was 9.64. The weight average molecular weight of the polymer measured by GPC was $2.2 \times 10^5$.

A filter material was prepared from the polymer in the same manner as in Example 1. The δ value of the filter supporting body was 10.30, the average fiber diameter of the filter material was 2.7 µm, the density was 90 g/m$^2$, and the thickness was 0.42 mm.

Using the obtained filter material, the elution test and the blood performance test were carried out in the same manner as in Example 1. The filled solution after sterilization and preservation was turbid, confirming that the polymer eluted during sterilization and preservation. The maximum absorbance of the filled solution was measured using an ultraviolet spectrophotometer at a wavelength of 220 nm to 350 nm to find that the maximum absorbance was 5.0 or more. The leukocyte removal rate was 99.5% and the platelet recovery rate was 52.0%.

Comparative Example 3

A polymer was synthesized in the same manner as in Example 1, except for using 5.0 mol % of MDG, 50.0 mol % of MMA, and 45.0 mol % of HBMA. The composition of the resulting polymer was analyzed from the integral value of NMR measurement, confirming that the composition was almost in agreement with the charged monomer composition. The δ value of the polymer was calculated according to the Fedors method to confirm that the δ value was 10.89. The weight average molecular weight of the polymer measured by GPC was $1.2 \times 10^5$.

1 g of the polymer obtained was dissolved in 100 ml of a mixed solvent of ethanol and purified water (70:30). A nonwoven fabric made from cellulose was immersed in the solvent. After removing excessive liquid, the nonwoven fabric was dried at room temperature for 16 hours to obtain the target filter. The δ value of the filter supporting body was 15.65, the average fiber diameter of the filter material was 4.1 µm, the density was 18 g/m$^2$, and the thickness was 0.1 mm.

Using the prepared filter material, the elution test was carried out in the same manner as in Example 1. The filled solution after sterilization and preservation was turbid, confirming that the polymer eluted during sterilization and preservation. The maximum absorbance of the filled solution was measured using an ultraviolet spectrophotometer at a wavelength of 220 nm to 350 nm to find that the maximum absorbance was 5.0 or more.

The filter material prepared in the above was cut into disks, each with a diameter of 6.8 mm. 28 sheets of the disks were laminated in a 1 ml column having an inlet port and an outlet port. The blood performance test was carried out in the same manner as in Example 1. The leukocyte removal rate was 85.1% and the platelet recovery rate 45.4%, confirming rather low recovery rate of platelets.

Comparative Example 4

A polymer was synthesized in the same manner as in Example 1, except for using 90.0 mol % of MDG and 10.0 mol % of MMA. The composition of the resulting polymer was analyzed from the integral value of NMR measurement, confirming that the composition was almost in agreement with the charged monomer composition. The δ value of the polymer was calculated according to the Fedors method to confirm that the δ value was 9.70. The weight average molecular weight of the polymer measured by GPC was $3.5 \times 10^5$.

A filter material was prepared from the polymer in the same manner as in Example 1. The δ value of the filter supporting body was 10.30, the average fiber diameter of the filter material was 2.7 µm, the density was 90 g/m$^2$, and the thickness was 0.42 mm.

Using the obtained filter material, the elution test and the blood performance test were carried out in the same manner as in Example 1. The filled solution after sterilization and preservation was turbid, confirming that the polymer eluted during sterilization and preservation. The maximum absorbance of the filled solution was measured using an ultraviolet spectrophotometer at a wavelength of 220 nm to 350 nm to find that the maximum absorbance was 5.0 or more. The leukocyte removal rate was 97.0% and the platelet recovery rate was 78.0%.

Comparative Example 5

A polymer was synthesized in the same manner as in Example 1, except for using 40.0 mol % of MDG, 25.0 mol % of MMA, and 35.0 mol % of HBMA. The composition of the resulting polymer was analyzed from the integral value of NMR measurement, confirming that the composition was almost in agreement with the charged monomer composition. The δ value of the polymer was calculated according to the Fedors method to confirm that the δ value was 10.58. The weight average molecular weight of the polymer measured by GPC was $4.2 \times 10^5$.

A filter material was prepared from the polymer in the same manner as in Example 1. The δ value of the filter supporting body was 10.30, the average fiber diameter of the filter material was 2.7 µm, the density was 90 g/m$^2$, and the thickness was 0.42 mm.

Using the obtained filter material, the elution test and the blood performance test were carried out in the same manner as in Example 1. The filled solution after sterilization and preservation was turbid, confirming that the polymer eluted during sterilization and preservation. The maximum absorbance of the filled solution was measured using an ultraviolet spectrophotometer at a wavelength of 220 nm to 350 nm to find that the maximum absorbance was 2.3. The leukocyte removal rate was 85.8% and the platelet recovery rate was 72.7%.

Example 6

Polymerization was carried out at 70° C. for six hours using 2.3 g (12 mmol) of MDG monomer, 2.0 g (20 mmol) of MMA monomer, and 1.3 g (8 mmol) of HBMA monomer (MDG: MMA:HBMA=30:50:20, in molar ratio), 300 ml of ethanol, and 0.1 g of V-65. The obtained reaction mixture was added dropwise to 10 l of water while stirring to cause the polymer to precipitate and the polymer was recovered as water-insoluble substance. The composition of the resulting polymer was analyzed from the integral value of NMR measurement, confirming that the composition was almost in agreement with the charged monomer composition. The δ value of the polymer was calculated according to the Fedors method to confirm that the δ value was 10.29. The weight average molecular weight of the polymer measured by GPC was $4.0 \times 10^4$.

1 g of the polymer thus obtained was dissolved in 99 g of a 70% aqueous solution of ethanol to obtain a 1% coating solution. 1 g of a nonwoven fabric made from polyethylene terephthalate was immersed in 10 ml of the 1% coating solution and dried at 25° C. for 12 hours to obtain a filter material. The δ value of the filter supporting body was 10.30, the average fiber diameter of the filter material was 2.9 μm, the density was 90 g/m², and the thickness was 0.40 mm.

Using the obtained filter material, the elution test and the blood performance test were carried out in the same manner as in Example 1. The appearance of the filled solution after sterilization and preservation was transparent and colorless. The maximum absorbance of the filled solution measured using an ultraviolet spectrophotometer at a wavelength of 220 nm to 350 nm was 0.41, indicating elution of a small amount of the polymer. The leukocyte removal rate was 95.1% and the platelet recovery rate was 74.3%.

The results are summarized in Table 1.

100 ml of a mixed solvent of ethanol and purified water (70:30). The polymer retained by the filter material was measured to find that the filter material contained was 20 wt % of the polymer as compared with 2 wt % in the filter material of Example 1. The amount of the polymer retained by the filter material was calculated from the weight change of the filter material before and after coating.

Using the obtained filter material, the elution test and the blood performance test were carried out in the same manner as in Example 1. The appearance of the filled solution after sterilization and preservation was transparent and colorless. The maximum absorbance of the filled solution was measured using an ultraviolet spectrophotometer at a wavelength of 220 nm to 350 nm to find that the maximum absorbance was 0.21. As a result, the leukocyte removal rate was 92.3% and the platelet recovery rate 82.1%, confirming the selective leukocyte removal capability.

Example 8

(Preparation of Selective Leukocyte Removal Filter Apparatus)

Next, a method of preparing the selective leukocyte removal filter apparatus used in the method for selectively

TABLE 1

| | Example | | | | | | Comparative Example | | | | |
|---|---|---|---|---|---|---|---|---|---|---|---|
| | 1 | 2 | 3 | 4 | 5 | 6 | 1 | 2 | 3 | 4 | 5 |
| Polymerizable monomer having polyalkylene oxide chain (mol %) | 30 | 40 | 20 | 20 | 15 | 30 | 5 | 65 | 5 | 90 | 40 |
| Polymerizable monomer having a hydrophobic group (mol %) | 50 | 50 | 60 | 50 | 40 | 50 | 5 | 35 | 50 | 10 | 25 |
| Polymerizable monomer having hydroxyl group (mol %) | 20 | 10 | 20 | 30 | 45 | 20 | 90 | 0 | 45 | 0 | 35 |
| Weight average molecular weight of polymer | $6.8 \times 10^5$ | $8.7 \times 10^5$ | $9.2 \times 10^5$ | $1.1 \times 10^5$ | $7.2 \times 10^5$ | $4.0 \times 10^4$ | $3.2 \times 10^5$ | $2.2 \times 10^5$ | $1.2 \times 10^5$ | $3.5 \times 10^5$ | $4.2 \times 10^5$ |
| δ-Value of polymer | 10.29 | 10.04 | 10.31 | 10.46 | 10.86 | 10.29 | 12.39 | 9.64 | 10.89 | 9.70 | 10.58 |
| δ-Value of filter supporting body | 10.30 | 10.30 | 7.90 | 10.30 | 10.30 | 10.30 | 10.30 | 10.30 | 15.65 | 10.30 | 10.30 |
| Elution test: | | | | | | | | | | | |
| Filling solution appearance * | Tp | Tp | Tp | Tp | Tp | Tp | Cl | Cl | Cl | Cl | Cl |
| $UV_{max(220-350\ nm)}$ | 0.04 | 0.05 | 0.08 | 0.08 | 0.15 | 0.41 | 2.4 | >5.0 | >5.0 | >5.0 | >2.3 |
| Blood performance test: | | | | | | | | | | | |
| Leukocyte removal rate (%) | 97.5 | 97.0 | 98.5 | 93.8 | 82.2 | 95.1 | 93.3 | 99.5 | 85.1 | 97.0 | 85.8 |
| Platelet recovery rate (%) | 85.0 | 85.0 | 89.4 | 83.7 | 80.2 | 74.3 | 3.1 | 52.0 | 45.4 | 78.0 | 72.7 |

* Tp: Transparent, Cl: Cloudy

As can be seen from Table 1, the filter materials using a polymer comprising a unit originating from a polymerizable monomer having a polyalkylene oxide chain, a unit originating from a polymerizable monomer having a hydrophobic group, and a unit originating from a polymerizable monomer having a hydroxyl group at a specific ratio were confirmed to elute only a minimal amount of polymer components and to exhibit selective leukocyte removal capability. On the other hand, the filter materials using a polymer not satisfying these conditions did not satisfy either the elution test or the blood performance test, or both. Furthermore, the filter material using a polymer with a weight average molecular weight of 100,000 or more was found to achieve excellent results in the eluting test.

Example 7

The filter material was prepared in the same manner as in Example 1, except that 10 g of the polymer was dissolved in removing leukocytes will be described. 4.0 g of the polymer obtained in Example 1 was dissolved in 500 ml of a mixed solvent of ethanol and purified water (70:30). A nonwoven fabric made from polyethylene terephthalate with an average fiber diameter of 2.7 μm, a density of 90 g/m², and a thickness of 0.42 mm was immersed in the solvent. After removing excessive liquid, the nonwoven fabric was dried at room temperature for 16 hours to obtain a filter material (A). 0.5 g of the polymer obtained in Example 1 was dissolved in 500 ml of a mixed solvent of ethanol and purified water (70:30). A nonwoven fabric made from polyethylene terephthalate with an average fiber diameter of 12 μm, a density of 30 g/m², and a thickness of 0.20 mm was immersed in the solvent. After removing excessive liquid, the nonwoven fabric was dried at room temperature for 16 hours to obtain a filter material (B).

The filter material (A) was cut into a sheet (width: 150 m, length: 250 mm) and the sheet was wound around a cylindrical polyethylene mesh with a diameter of 28 mm. The filter material (B) cut into a rectangle of 150 mm×1,660 mm was wound around the cylinder and laminated over the filter material (A). A polyethylene mesh with a width of 150 mm and a length of 130 mm was further wound around the filter material (B) to obtain a hollow cylindrical filter. After sealing both ends by polyurethane, the cylinder was placed in a cylindrical polycarbonate container with an internal diameter of 41 mm of which the top and the bottom were respectively provided with a blood inlet port and a blood outlet port, so that the outer circumference of the cylinder was connected to the blood inlet port of the container and the inner circumference of the cylinder was connected to the blood outlet port of the container. The container was filled with a physiological saline solution and sterilized with δ-ray (irradiation dose: 25 kGy) to prepare a selective leukocyte removal filter apparatus. In the selective leukocyte removal filter apparatus, the filling density of the filter material was 0.157 g/cm$^3$, the filtration area of the first blood contact layer was 174 cm$^2$, the volume standard specific surface area of the first blood contact layer was 0.33 m$^2$/ml, the volume standard specific surface area of the second blood contact layer was 1.5 m$^2$/ml, the laminated layer thickness ratio of the first blood contact layer to the second blood contact layer was 4.0, and the thickness of the hollow cylindrical filter was 4.5 mm.

(Method of Extracorporeal Circulation Using Selective Leukocyte Removal System)

A selective leukocyte removal system for treating blood of a patient of ulcerative colitis shown in FIG. 2 was prepared. Extracorporeal circulation, each treatment being for one hour at a flow rate of 50 ml/min, was conducted five times for each patient at a frequency of once a week using the selective leukocyte removal system in which the above filter apparatus was used. As an anticoagulant solution, a mixture of 3,000 units of heparin and 500 ml of a physiological saline solution was continuously injected at a flow rate of 8 ml/min.

At 30 minutes after initiation of extracorporeal circulation, blood samples were recovered at locations before and after the selective leukocyte removal means to determine the leukocyte concentration and platelet concentration using an automatic blood cell counter. The leukocyte removal rate and the platelet recovery rate were calculated from the found concentrations. As a result, the leukocyte removal rate was 82% and the platelet recovery rate was 65%. A high platelet recovery rate was attained. After 5 treatments, the number of diarrhea occurrences of the patient decreased from 11 times/day to 4 times/day, confirming improvement of the symptom.

Example 9

A selective leukocyte removal system for treating blood of a patient of rheumatism shown in FIG. 2 was prepared. Extracorporeal circulation, each treatment being for one hour at a flow rate of 50 ml/min, was conducted seven times for each patient at a frequency of once a week using the selective leukocyte removal system in which the filter apparatus of Example 8 was used. As an anticoagulant solution, a mixture of 250 ml of ACD-A solution and 250 ml of a physiological saline solution was continuously injected at a flow rate of 8 ml/min.

At 30 minutes after initiation of extracorporeal circulation, blood samples were recovered at locations before and after the selective leukocyte removal means to determine the leukocyte concentration and platelet concentration using an automatic blood cell counter. The leukocyte removal rate and the platelet recovery rate were calculated from the found concentrations. As a result, the leukocyte removal rate was 75% and the platelet recovery rate was 82%. A high platelet recovery rate was attained. The Ritchie index (see Ritchie Index, Index to evaluate the conditions of articular rheumatism patient, Ritchie et al. *Quarterly Journal of Medicine*, New Series XXXVII, No. 147, p. 393-406, July 1968) of the patient after 7 treatments decreased from 15 points to 8 points, showing improvement in the symptom.

Example 10

The filter material (B) of Example 8 was cut into a sheet (width: 150 mm, length: 1,500 mm) and the sheet was wound around a cylindrical mesh with a diameter of 31 mm made from polyethylene. A polyethylene mesh with a width of 150 mm and a length of 130 mm was further wound around the filter material (B) to obtain a hollow cylindrical filter. A selective leukocyte removal filter apparatus was prepared in the same manner as in Example 8. In the selective leukocyte removal filter apparatus, the filling density of the filter material was 0.145 g/cm$^3$, the filtration area of the first blood contact layer was 174 cm$^2$, the volume standard specific surface area of the first blood contact layer was 0.33 m$^2$/ml, and the thickness of the hollow cylindrical filter was 3.0 mm.

A selective leukocyte removal system for treating blood of a patient of systemic inflammatory response syndrome shown in FIG. 2 was prepared. Extracorporeal circulation for one hour at a flow rate of 50 ml/min was conducted for the patient using the selective leukocyte removal system in which the above filter apparatus was used. As an anticoagulant solution, a mixture of 3,000 units of heparin and 500 ml of a physiological saline solution was continuously injected at a flow rate of 8 ml/min.

At 30 minutes after initiation of extracorporeal circulation, blood samples were recovered at locations before and after the selective leukocyte removal means to determine the leukocyte concentration and platelet concentration using an automatic blood cell counter. The leukocyte removal rate and the platelet recovery rate were calculated from the found concentrations. As a result, the leukocyte removal rate was 58% and the platelet recovery rate was 92%. A high platelet recovery rate was attained. Moreover, TNF-α production capability originating from culture supernatant of the mononuclear cell in the patient's peripheral blood before and after the treatment was determined. For determining the TNF-α production capability, a mononuclear cell layer was separated from the blood using a Conray-Ficoll solution, the cells were stimulated with Concanavarin A (Con A) at a final concentration of 7 mg/ml per 1×10$^6$ mononuclear cells, then the cells were cultured for 24 hours to measure the TNF-α concentration of the supernatant. As a result, the concentration of 9,100 pg/ml before the treatment decreased to 4,800 pg/ml after the treatment, confirming suppression of the disease. Since TNF-α activates leukocytes (neutrophil leucocytes) and induces a tissue damage, the decrease in the concentration is supposed to improve the inflammation symptom.

INDUSTRIAL APPLICABILITY

As is clear from the above description, the present invention provides a polymer excelling in biocompatibility, exhibiting, in particular, only a low adsorption to platelets, and having a low elution property. The filter material for selectively removing leukocytes, the selective leukocyte removal filter apparatus, and the selective leukocyte removal system using the biocompatible polymer can selectively remove leukocytes from various bloods, particularly from whole blood, while inhibiting adsorption of platelets, and are useful for platelet transfusion and extracorporeal circulation for leukocyte removal.

The invention claimed is:

1. A selective leukocyte removal filter material comprising: a biocompatible nonionic polymer and a supporting body, wherein a biocompatible nonionic polymer is polymerized from units comprising 8-45 mol % of a polymerizable monomer having a polyalkylene oxide chain, 30-90 mol % of a polymerizable monomer having a hydrophobic group, and 2-50 mol % of a polymerizable monomer having a hydroxyl group, and wherein the biocompatible nonionic polymer is present on at least the surface of the supporting body.

2. A selective leukocyte removal filter material according to claim 1, wherein the polymer has a weight average molecular weight of 100,000 to 3,000,000.

3. A selective leukocyte removal filter material according to claim 1, wherein the molar content ratio of the unit originating from the polymerizable monomer having a hydroxyl group to the unit originating from the polymerizable monomer having a hydrophobic group is from 0.05 to 1.

4. A selective leukocyte removal filter material according to claim 1, wherein the polymerizable monomer having a hydroxyl group has solubility in water at 20° C. in the range from 3 wt % to less than 50 wt %.

5. A selective leukocyte removal filter material according to claim 4, wherein the polymerizable monomer having a hydroxyl group is 2-hydroxyisobutyl (meth) acrylate.

6. The selective leukocyte removal filter material according to claim 1, wherein the polymer has a solubility parameter (δ value) of 10.0 to 11.5 and the filter supporting body has a solubility parameter (δ value) of 7.0 to 15.0.

7. The filter material according to claim 1, wherein the amount of the polymer held on the filter supporting body is 0.001 wt % to less than 10 wt %.

8. The filter material according to claim 1, wherein the polymer coating rate of the filter supporting body is from 40% to 90%.

9. The filter material according to claim 1, wherein the filter material is a woven fabric or nonwoven fabric.

10. The filter material according to claim 9, wherein the average fiber diameter of the woven or nonwoven fabric is from 0.5 μm to 50 μm and the filling density is from 0.05 g/cm$^3$ to 0.5 g/cm$^3$.

11. The selective leukocyte removal filter material according to claim 1, used for selectively removing leukocytes from blood extracted from a patient of cellular immune abnormality.

12. The selective leukocyte removal filter material according to claim 11, wherein the disease is chronic or malignant rheumatoid arthritis, systemic erythematodes, Behcet's disease, idiopathic thrombo cytopenic purpura, autoimmune hepatitis, ulcerative colitis, Crohn's disease, atopic dermatitis, rapidly progressive glomerulonephritis, or systemic inflammatory response syndrome.

13. A selective leukocyte removal filter apparatus comprising the filter material according to claim 1, packed in a container having at least a blood inlet port and a blood outlet port.

14. The selective leukocyte removal filter apparatus according to claim 13, wherein a hollow cylindrical filter formed from the filter material wound in the shape of a cylinder is packed in the container with both ends sealed, and either the blood inlet port or the blood outlet port is provided communicating with either the inner perimeter or the outer perimeter of the cylindrical filter material.

15. The selective leukocyte removal filter apparatus according to claim 14, wherein the hollow cylindrical filter has a configuration of a scroll of a laminated body made of a) the filter material in the form of a sheet and b) a spacer layer material in the form of a sheet allowing blood to pass through, the starting and/or terminal ends of the spacer layer rolled in the form of a scroll being open to the outer perimeter and/or the inner perimeter of the hollow cylindrical filter to provide a passage for blood.

16. The selective leukocyte removal filter apparatus according to claim 14, wherein the hollow cylindrical filter has a first blood contact layer with an area from 50 cm$^2$ to 1,000 cm$^2$.

17. The selective leukocyte removal filter apparatus according to claim 16, wherein the volume standard specific surface area of the first blood contact layer is 0.08 m$^{2}$/ml to less than 1.0 m$^{2}$/ml.

18. A selective leukocyte removal filter apparatus comprising:
a hollow cylindrical filter formed from a selective leukocyte removal filter material wound in the shape of a cylinder,
the hollow cylindrical filter being packed in a container having two sealed ends, at least a blood inlet port and a blood outlet port,
either the blood inlet port or the blood outlet port being in fluid communication with either the inner perimeter or the outer perimeter of the cylindrical filter material, and the hollow cylindrical filter having
(i) a first blood contact layer with an area from 50 cm$^2$ to 1,000 cm$^2$ having a volume standard specific surface area of 0.08 m$^{2}$/ml to less than 1.0 m$^{2}$/ml and
(ii) a second blood contact layer with a volume standard specific surface area of 1.0 m$^{2}$/ml to less than 20 m$^{2}$/ml,
the selective leukocyte removal filter material comprising a supporting body, and a biocompatible nonionic polymer present on at least one surface of the supporting body, wherein the biocompatible nonionic polymer is polymerized from units comprises:
8-45 mol % of a polymerizable monomer having a polyalkylene oxide chain,
30-90 mol % of a polymerizable monomer having a hydrophobic group and
2-50 mol % of a polymerizable monomer having a hydroxyl group.

19. The selective leukocyte removal filter apparatus according to claim 18, wherein the thickness ratio of the second blood contact layer to the first blood contact layer is from 0.2 to 10.0.

20. The selective leukocyte removal filter apparatus according to claim 14, wherein the thickness of the hollow cylindrical filter is from 0.6 mm to 12.0 mm.

21. The selective leukocyte removal filter apparatus according to claim 13, wherein the filter material is maintained under the condition of the saturated moisture content or more using water or an aqueous solution of a water-soluble substance with a minimal risk of damage to living bodies and is sterilized.

22. The selective leukocyte removal filter apparatus according to claim 21, wherein the concentration of the water-soluble substance in the aqueous solution is 5 wt % or less.

23. The selective leukocyte removal filter apparatus according to claim 21, wherein the water-soluble substance is sodium chloride.

24. The selective leukocyte removal filter apparatus according to claim 13, used for selectively removing leukocytes from blood extracted from a patient of cellular immune abnormality.

25. The selective leukocyte removal filter apparatus according to claim 24, wherein the disease is chronic or malignant rheumatoid arthritis, systemic erythematodes, Behcet's disease, idiopathic thrombo cytopenic purpura, autoimmune hepatitis, ulcerative colitis, Crohn's disease, atopic dermatitis, rapidly progressive glomerulonephritis, or systemic inflammatory response syndrome.

26. A selective leukocyte removal system comprising a blood delivery means, an anticoagulant fluid injection means, and a selective leukocyte removal means, wherein the selective leukocyte removal means comprises the selective leukocyte removal filter apparatus according to claim 13.

27. The selective leukocyte removal system according to claim 26, wherein the blood delivery means delivers blood in a quantity from 1 l to 10 l at a flow rate of 10 ml/mm to 200 ml/min.

28. The selective leukocyte removal system according to claim 26, wherein the anticoagulant fluid injection means injects an anticoagulant fluid at a rate of 1% to 20% of the blood flow rate.

29. The selective leukocyte removal system according to claim 26, wherein the anticoagulant fluid injected from the anticoagulant fluid injection means comprises heparin or a low molecular weight heparin.

30. The selective leukocyte removal system according to claim 26, wherein the anticoagulant fluid injected from the anticoagulant fluid injection means comprises a protease inhibitor.

31. The selective leukocyte removal system according to claim 26, wherein the anticoagulant fluid injected from the anticoagulant fluid injection means comprises an ACD-A solution or an ACD-B solution.

32. The selective leukocyte removal system according to claim 29, wherein the amount of anticoagulant fluid injected is from 100 units to 2,000 units per 1 l of blood.

33. The selective leukocyte removal system according to claim 30, wherein the amount of anticoagulant fluid injected is from 2 mg to 40 mg per 1 l of blood.

34. The selective leukocyte removal system according to claim 31, wherein the amount of anticoagulant fluid injected is from 20 ml to 160 ml per 1 l of blood.

35. The selective leukocyte removal system according to claim 26, used for selectively removing leukocytes from blood extracted from a patient of cellular immune abnormality.

36. The selective leukocyte removal system according to claim 35, wherein the disease is chronic or malignant rheumatoid arthritis, systemic erythematodes, Behcet's disease, idiopathic thrombo cytopenic purpura, autoimmune hepatitis, ulcerative colitis, Crohn's disease, atopic dermatitis, rapidly progressive glomerulonephritis, or systemic inflammatory response syndrome.

* * * * *